(12) United States Patent
Houben et al.

(10) Patent No.: US 8,271,072 B2
(45) Date of Patent: Sep. 18, 2012

(54) DETECTING WORSENING HEART FAILURE

(75) Inventors: Richard P M Houben, Lanaken (BE); Roger Kessels, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 358 days.

(21) Appl. No.: 12/768,384

(22) Filed: Apr. 27, 2010

(65) Prior Publication Data

US 2011/0105860 A1    May 5, 2011

Related U.S. Application Data

(60) Provisional application No. 61/256,683, filed on Oct. 30, 2009.

(51) Int. Cl.
*A61B 5/0205* (2006.01)

(52) U.S. Cl. ......... 600/513; 600/301; 600/519; 128/923

(58) Field of Classification Search .................. None
See application file for complete search history.

(56) References Cited

U.S. PATENT DOCUMENTS

| | | | |
|---|---|---|---|
| 4,374,382 A | 2/1983 | Markowitz | |
| 4,823,797 A | 4/1989 | Heinze et al. | |
| 5,107,833 A | 4/1992 | Barsness | |
| 5,117,824 A | 6/1992 | Keimel et al. | |
| 5,168,871 A | 12/1992 | Grevious | |
| 5,271,395 A | 12/1993 | Wahlstrand et al. | |
| 5,292,343 A | 3/1994 | Blanchette et al. | |
| 5,314,450 A | 5/1994 | Thompson | |
| 5,324,315 A | 6/1994 | Grevious | |
| 5,354,319 A | 10/1994 | Wyborny et al. | |
| 5,383,909 A | 1/1995 | Keimel | |
| 5,545,186 A | 8/1996 | Olson et al. | |
| 5,749,367 A * | 5/1998 | Gamlyn et al. | ............... 600/509 |
| 5,755,736 A | 5/1998 | Gillberg et al. | |
| 5,836,975 A | 11/1998 | DeGroot | |
| 5,876,353 A | 3/1999 | Riff | |
| 5,957,861 A | 9/1999 | Combs et al. | |
| 6,045,513 A | 4/2000 | Stone et al. | |
| 6,102,874 A | 8/2000 | Stone et al. | |
| 6,104,949 A | 8/2000 | Crick et al. | |
| 6,148,233 A | 11/2000 | Owen et al. | |

(Continued)

FOREIGN PATENT DOCUMENTS

DE    10148440 A1    4/2003

(Continued)

OTHER PUBLICATIONS

Reply to Written Opinion mailed Feb. 4, 2011, from international application No. PCT/US2010/054539, dated Aug. 30, 2011, 5 pp.

(Continued)

*Primary Examiner* — Kennedy Schaetzle
(74) *Attorney, Agent, or Firm* — Michael C. Soldner

(57) ABSTRACT

A method comprises monitoring a heart rate, a respiration rate and an activity level of a patient, comparing the monitored heart rate, respiration rate and activity level to a predetermined threshold zone which is a function of heart rate, respiration rate and activity level, determining the patient is experiencing worsening heart failure when the monitored heart rate, respiration rate and activity level are outside the predetermined threshold zone; and after determining the patient is experiencing worsening heart failure when the monitored heart rate, respiration rate and activity level are outside the predetermined threshold zone, issuing an alert to indicate that the patient is experiencing worsening heart failure.

20 Claims, 9 Drawing Sheets

U.S. PATENT DOCUMENTS

| | | | |
|---|---|---|---|
| 6,154,674 | A | 11/2000 | Meier |
| 6,221,011 | B1 | 4/2001 | Bardy |
| 6,263,243 | B1 | 7/2001 | Lang |
| 6,277,072 | B1 | 8/2001 | Bardy |
| 6,280,380 | B1 | 8/2001 | Bardy |
| 6,280,409 | B1 | 8/2001 | Stone et al. |
| 6,336,903 | B1 | 1/2002 | Bardy |
| 6,405,085 | B1 | 6/2002 | Graupner et al. |
| 6,449,509 | B1 | 9/2002 | Park et al. |
| 6,459,929 | B1 | 10/2002 | Hopper et al. |
| 6,463,326 | B1 | 10/2002 | Hartley et al. |
| 6,473,640 | B1 | 10/2002 | Erlebacher |
| 6,480,733 | B1 | 11/2002 | Turcott |
| 6,512,949 | B1 | 1/2003 | Combs et al. |
| 6,572,557 | B2 | 6/2003 | Tchou et al. |
| 6,595,927 | B2 | 7/2003 | Pitts-Crick et al. |
| 6,671,549 | B2 | 12/2003 | Van Dam et al. |
| 6,821,249 | B2 | 11/2004 | Casscells, III et al. |
| 6,866,629 | B2 | 3/2005 | Bardy |
| 6,895,275 | B2 | 5/2005 | Markowitz et al. |
| 6,907,288 | B2 | 6/2005 | Daum |
| 6,931,272 | B2 | 8/2005 | Burnes |
| 6,945,934 | B2 | 9/2005 | Bardy |
| 6,960,167 | B2 | 11/2005 | Bardy |
| 7,127,290 | B2 | 10/2006 | Girouard et al. |
| 7,177,681 | B2 | 2/2007 | Zhu et al. |
| 7,184,821 | B2 | 2/2007 | Belalcazar et al. |
| 7,248,916 | B2 | 7/2007 | Bardy |
| 7,272,442 | B2 | 9/2007 | Freeberg |
| 7,308,309 | B1 | 12/2007 | Koh |
| 7,310,551 | B1 | 12/2007 | Koh et al. |
| 7,313,434 | B2 | 12/2007 | Belalcazar et al. |
| 7,340,296 | B2 | 3/2008 | Stahmann et al. |
| 7,387,610 | B2 | 6/2008 | Stahmann et al. |
| 7,389,143 | B2 | 6/2008 | Hopper et al. |
| 8,180,440 | B2 * | 5/2012 | McCombie et al. ........ 600/513 |
| 2001/0011153 | A1 | 8/2001 | Bardy |
| 2001/0021801 | A1 | 9/2001 | Bardy |
| 2001/0039504 | A1 | 11/2001 | Linberg et al. |
| 2002/0026104 | A1 | 2/2002 | Bardy |
| 2003/0028221 | A1 | 2/2003 | Zhu et al. |
| 2003/0055461 | A1 | 3/2003 | Girouard et al. |
| 2003/0125611 | A1 | 7/2003 | Bardy |
| 2003/0149367 | A1 | 8/2003 | Kroll et al. |
| 2003/0220580 | A1 | 11/2003 | Alt |
| 2004/0102712 | A1 | 5/2004 | Belalcazar et al. |
| 2004/0122484 | A1 | 6/2004 | Hatlestad et al. |
| 2004/0148140 | A1 * | 7/2004 | Tarassenko et al. ........ 702/189 |
| 2004/0167580 | A1 | 8/2004 | Mann et al. |
| 2004/0172080 | A1 | 9/2004 | Stadler et al. |
| 2005/0124908 | A1 | 6/2005 | Belalcazar et al. |
| 2006/0020295 | A1 | 1/2006 | Brockway et al. |
| 2006/0094967 | A1 * | 5/2006 | Bennett et al. ............. 600/508 |
| 2006/0293609 | A1 | 12/2006 | Stahmann et al. |
| 2007/0021678 | A1 * | 1/2007 | Beck et al. ................. 600/510 |
| 2007/0142732 | A1 | 6/2007 | Brockway et al. |
| 2007/0156061 | A1 | 7/2007 | Hess |
| 2007/0203423 | A1 * | 8/2007 | Bardy .......................... 600/529 |
| 2008/0024293 | A1 | 1/2008 | Stylos |
| 2008/0027349 | A1 | 1/2008 | Stylos |
| 2008/0082001 | A1 * | 4/2008 | Hatlestad et al. ........... 600/481 |
| 2008/0161657 | A1 | 7/2008 | Bullens et al. |
| 2010/0030292 | A1 | 2/2010 | Sarkar et al. |
| 2010/0030293 | A1 | 2/2010 | Sarkar et al. |
| 2010/0114241 | A1 | 5/2010 | Donofrio et al. |
| 2010/0198097 | A1 | 8/2010 | Sowelam |

FOREIGN PATENT DOCUMENTS

| | | |
|---|---|---|
| EP | 1997427 A1 | 12/2008 |
| WO | 9833554 A1 | 8/1998 |
| WO | 2000064336 A1 | 11/2000 |
| WO | 2001032260 A1 | 5/2001 |
| WO | 2006/070124 A1 | 7/2006 |
| WO | 2006/081432 A1 | 8/2006 |
| WO | 2007/079354 A2 | 7/2007 |

OTHER PUBLICATIONS

Written Opinion of international application No. PCT/US2010/054539, dated Oct. 26, 2011, 6 pp.

Office Action from U.S. Appl. No. 12/184,003, dated Dec. 21, 2011, 11 pp.

Office Action from U.S. Appl. No. 12/184,149, dated Sep. 30, 2011, 6 pp.

Response to Office Action dated Sep. 30, 2011, from U.S. Appl. No. 12/184,149, filed Dec. 12, 2011, 14 pp.

Office Action from U.S. Appl. No. 12/363,264, dated Nov. 30, 2011, 5 pp.

International Preliminary Report on Patentability from international application No. PCT/US2010/054539, dated Jan. 26, 2012, 6 pp.

Response to Office Action dated Dec. 21, 2011, from U.S. Appl. No. 12/184,003, filed Feb. 21, 2012, 7 pp.

Office Action from U.S. Appl. No. 12/184,149, dated Jan. 27, 2012, 7 pp.

Response to Office Action dated Nov. 30, 2011, from U.S. Appl. No. 12/363,264, filed Feb. 29, 2012, 9 pp.

Response to Office Action dated Jan. 27, 2012, from U.S. Appl. No. 12/184,149, filed Apr. 25, 2012, 13 pp.

Adamson et al, "Continuous Autonomic Assessment in Patients with Symptomatic Heart Failure: Prognostic Value of Heart Rate Variability Measured by an Implanted Cardiac Resynchronization Device", Circulation Journal of American Heart Association, pp. 2389-2394, 110:16, Lippincott Williams & Wilkins, Baltimore MD, 2004.

Lusignan, et al. "Compliance and Effectiveness of 1 Year's Home Telemonitoring. The Report of a Pilot Study of Patients with Chronic Heart Failure" European Journal of Heart Failure, 3:723-730, 2001.

Baer, et al. "Electronic Home Monitoring of Congestive Heart Failure Patients: Design and Feasibility", Congestive Heart Failure, 5:105-113, 1999.

Wuerz et al., "Effects of Prehospital Medications on Mortality and Length of Stay in Congestive Heart Failure", Annals of Emergency Medicine 21:6 pp. 669-674, Jun. 1992.

Berman et al. "Transthoracic Electrical Impedance as a Guide to Intravascular Overload", Archives Surgery, 102, pp. 61-64 Jan. 1971.

U.S. Appl. No. 12/112,765, filed Apr. 30, 2008 by Todd M. Zielinski et al.

U.S. Appl. No. 12/609,700, filed Oct. 30, 2009 by Li Wang.

International Search Report and Written Opinion from corresponding PCT Application Serial No. PCT/US2010/054539 dated Feb. 4, 2011 (11 pages).

Office Action from U.S. Appl. No. 12/184,003, dated Jun. 28, 2011, 11 pp.

Response to Office Action dated Jun. 28, 2011, from U.S. Appl. No. 12/184,003, filed Sep. 28, 2011, 15 pp.

Office Action from U.S. Appl. No. 12/184,149, dated Apr. 7, 2011, 7 pp.

Response to Office Action dated Apr. 7, 2011, from U.S. Appl. No. 12/184,149, filed Jul. 7, 2011, 20 pp.

Office Action from U.S. Appl. No. 12/363,264, dated May 9, 2012, 9 pp.

\* cited by examiner

DETECTING WORSENING HEART FAILURE

This application claims the benefit of U.S. Provisional Application No. 61/256,683, filed Oct. 30, 2009, entitled, "DETECTING WORSENING HEART FAILURE," the entire content of which is incorporated herein by reference.

TECHNICAL FIELD

The invention relates to medical devices and, more particularly, devices for the detection of worsening heart failure and treatment of related ailments.

BACKGROUND

A variety of medical devices have been used or proposed for use to deliver a therapy to and/or monitor a physiological condition of patients. As examples, such medical devices may deliver therapy and/or monitor conditions associated with the heart, muscle, nerve, brain, stomach or other organs or tissue. Medical devices that deliver therapy include medical devices that deliver one or both of electrical stimulation or a therapeutic agent to the patient. Some medical devices are implantable medical devices (IMDs) that are implanted within the patient.

Some medical devices have been used or proposed for use to monitor heart failure or to detect heart failure events. Typically, such medical devices have been implantable and, in many cases, have been cardiac pacemakers or defibrillators, such as cardioverters, with added heart failure monitoring functionality. In some cases, such medical devices have monitored heart failure by monitoring intrathoracic impedance, which may provide a good indication of the level of pulmonary edema in patients. In other cases, medical devices have monitored pressure in the right ventricle of a patient using a pressure sensor, which can also provide an indication of the level of pulmonary edema in patients.

While pulmonary edema is a sign of many other conditions it is also a sign of worsening heart failure. Worsening heart failure may result in cardiac chamber dilation, increased pulmonary blood volume, and fluid retention in the lungs—all of which contribute to a decrease in intrathoracic impedance. Other diagnostic parameters, such as heart rate variability, have been proposed for use in such devices to identify worsening heart failure or heart failure events, such as decompensation. Decompensation is a condition in which the heart is unable to provide adequate cellular perfusion to all parts of the body, including the lungs, without assistance. Without treatment, decompensation is expected to result in the death of a patient due to heart/lung failure.

Generally, the first indication that a physician would have of the occurrence of decompensation in a patient is not until it becomes a physical manifestation with swelling or breathing difficulties so overwhelming as to be noticed by the patient who then proceeds to be examined by a physician. This is undesirable since hospitalization at such a time would likely be required for a heart failure patient. Accordingly, medical devices have been used to monitor impedance in patients and provide an alert to the patient to seek medical treatment prior to the onset of worsening heart failure with symptoms, such as pulmonary edema, that require hospitalization.

SUMMARY

In patients with chronic heart failure, early detection of an imminent episode of decompensation to prevent or shorten hospitalization is an ongoing challenge. Current detection of heart failure decompensation is based on intra-thoracic impedance measurement detecting fluid accumulation in the lungs. Detection of heart failure decompensation could also be based on estimation of the pulmonary artery pressure (ePAD) using an absolute pressure sensor positioned on a lead in the right ventricle (RV).

Functional impairment of the lungs due to fluid accumulation affects heart function, whereas functional impairment of the heart often affects lung function. This also leads to an increased heart rate and ventilatory effort for the patient at a given activity level.

In order to anticipate decompensation in a patient, the disclosed techniques include monitoring respiration rate, heart rate and activity level of a patient. If the patient is experiencing worsening heart failure, the respiration rate and heart rate will not be consistent with baseline heart rates and baseline respiration rates previously associated with the patient. The techniques may include using measured baseline heart rates and baseline respiration rates for a plurality of activity levels to define a predetermined threshold zone, and issuing an alert if the respiration rate, heart rate and activity level of a patient is outside the predetermined threshold zone.

An activity level of the patient can be obtained by a commonly used activity sensor (accelerometer), whereas heart rate can be obtained from intrinsic sinus beats detected from the intra-cardiac or subcutaneous (subQ) electrogram. Likewise, the ventilation rate can be obtained by measuring intrathoracic impedance. For example, respiration often appears as low-frequency "noise" on an unfiltered intra-cardiac electrogram.

In one example, a method comprises monitoring a heart rate, a respiration rate and an activity level of a patient, comparing the monitored heart rate, respiration rate and activity level to a predetermined threshold zone which is a function of heart rate, respiration rate and activity level, determining the patient is experiencing worsening heart failure when the monitored heart rate, respiration rate and activity level are outside the predetermined threshold zone; and after determining the patient is experiencing worsening heart failure when the monitored heart rate, respiration rate and activity level are outside the predetermined threshold zone, issuing an alert to indicate that the patient is experiencing worsening heart failure.

In another example, a medical system for monitoring a condition of a patient comprises one or more sensors configured to output one or more signals indicative of a heart rate, a respiration rate and an activity level of the patient, a memory configured to store an indication of a predetermined threshold zone which is a function of heart rate, respiration rate and activity level and a diagnostic unit configured to compare the monitored heart rate, respiration rate and activity level to the predetermined threshold zone, and determine the patient is experiencing worsening heart failure when the monitored heart rate, respiration rate and activity level are outside the predetermined threshold zone. The medical system further comprises an alert module configured to issue an alert to indicate that the patient is experiencing worsening heart failure after the diagnostic unit determines the patient is experiencing worsening heart failure when the monitored heart rate, respiration rate and activity level are outside the predetermined threshold zone.

In another example, a system comprises means for monitoring a heart rate of a patient, means for monitoring a respiration rate of the patient, means for monitoring an activity level of the patient, means for comparing the monitored heart rate, respiration rate and activity level to a predetermined threshold zone which is a function of heart rate, respiration rate and activity level, means for determining the patient is experiencing worsening heart failure when the monitored heart rate, respiration rate and activity level are outside the predetermined threshold zone and means for, after determining the patient is experiencing worsening heart failure when the monitored heart rate, respiration rate and activity level are outside the predetermined threshold zone, issuing an alert to indicate that the patient is experiencing worsening heart failure.

In another example, a computer readable storage medium comprises instructions that cause a processor to monitor a heart rate, a respiration rate and an activity level of a patient, compare the monitored heart rate, respiration rate and activity level to a predetermined threshold zone which is a function of heart rate, respiration rate and activity level, determine the patient is experiencing worsening heart failure when the monitored heart rate, respiration rate and activity level are outside the predetermined threshold zone, and after determining the patient is experiencing worsening heart failure when the monitored heart rate, respiration rate and activity level are outside the predetermined threshold zone, issue an alert to indicate that the patient is experiencing worsening heart failure.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
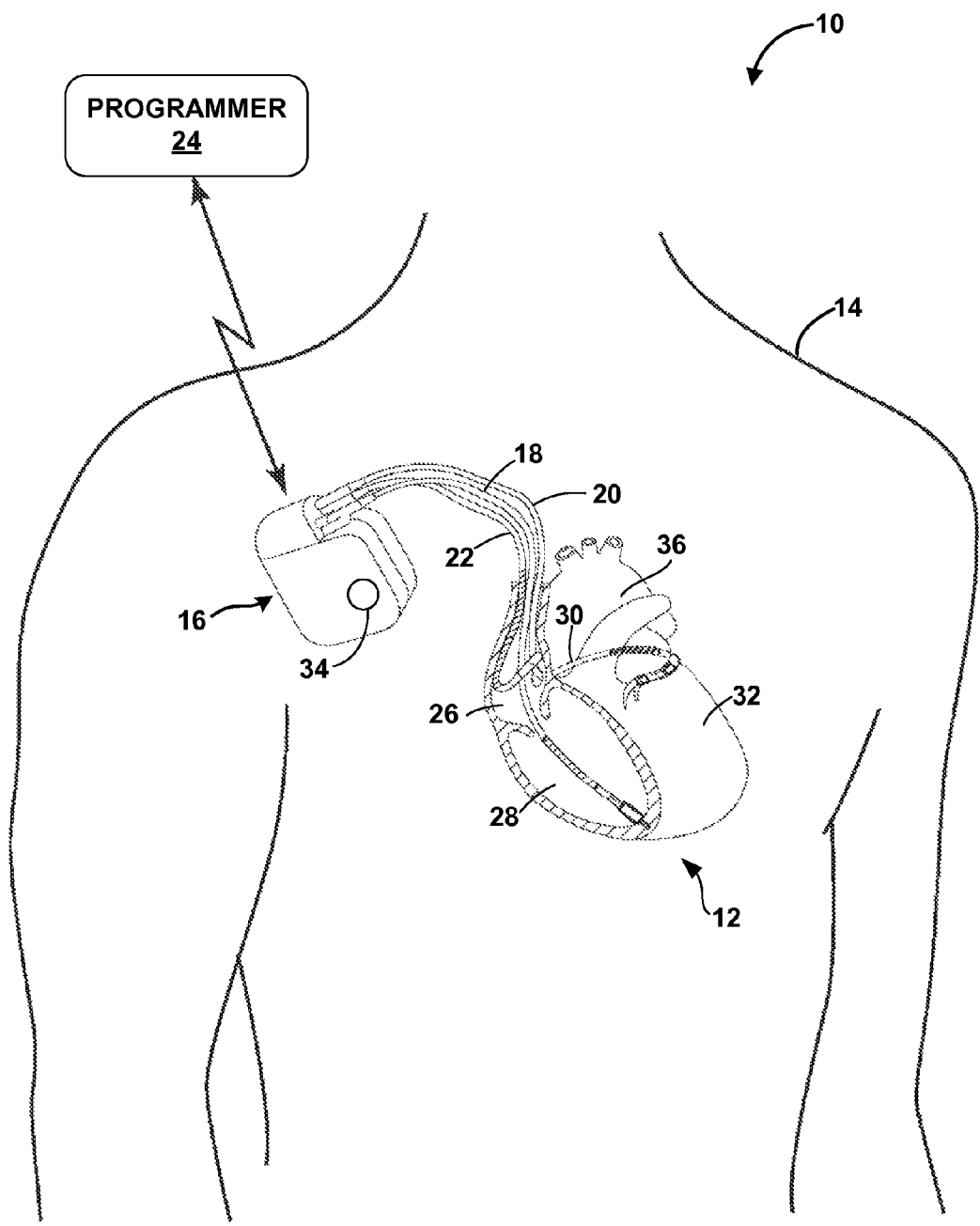
FIG. 1 is a conceptual diagram illustrating an example system that detects worsening heart failure using a predetermined threshold zone for the patient.

FIG. 1 is a conceptual diagram illustrating an example system 10 that may be used to determine worsening heart failure in patient 14 by measuring multiple diagnostic parameters and comparing them to predetermined levels associated with patient 14 for a given activity level. Patient 14 ordinarily, but not necessarily, will be a human. System 10 is configured to generate an alert in response to detecting worsening heart failure so that patient 14 can seek appropriate treatment before experiencing a heart failure hospitalization event such as decompensation. In addition or in the alternative, system 10 may alter patient therapy in response to detecting worsening heart failure. For example, system 10 may increase the charge level of a high voltage energy storage device used to deliver a defibrillation pulse to patient 14 in preparation for a heart failure event. As another example, system 10 may alter drug therapy to patient 14, such as delivering diuretics to patient 14. System 10 may also perform other suitable techniques to mitigate worsening heart failure.

System 10 includes implantable medical device (IMD) 16, which is coupled to leads 18, 20, and 22, an electrode 34 located on the can of IMD 16, and a programmer 24. In some examples, IMD 16 may be a purely diagnostic device that monitors multiple diagnostic parameters associated with heart failure as well as the activity level of patient 14. In other examples, IMD 16 may additionally operate as a therapy delivery device to deliver electrical signals to heart 12 via one or more of leads 18, 20, and 22, such as an implantable pacemaker, a cardioverter, and/or defibrillator. In some examples, IMD 16 may operate as a drug delivery device that delivers therapeutic substances to patient 14 via catheters (not shown), or as a combination therapy device that delivers both electrical signals and therapeutic substances. Moreover, IMD 16 is not limited to devices implanted as shown in FIG. 1. As an example, IMD 16 may be implanted subcutaneously in patient 14, or may be an entirely external device with leads attached to the skin of patient 14 or implanted percutaneously in patient 14. In some examples, IMD 16 need not include leads, but may include a plurality of electrodes, like electrode 34, on the housing of IMD 16.

In general, IMD 16 monitors a one or more parameters that are indicative of respiration rate, one or more parameters that are indicative of heart rate and one or more parameters that are indicative of an activity level of patient 14. IMD 16 detects worsening heart failure in patient 14 at least in part by comparing these measured parameters to predetermined levels associated with patient 14 for a given activity level.

IMD 16 includes at least one sensor that provides an output indicative of an activity level of patient 14. For example, as described in further detail with respect to FIG. 3, IMD 16 may include a 3-axis accelerometer, such as a piezoelectric and/or micro-electro-mechanical accelerometer that generates an output based on activity level. In addition, as described in further detail with respect to FIG. 2, IMD 16 uses electrode 34 and/or electrodes on one of leads 18, 20, and 22 to monitor heart rate, e.g., as part of an electrocardiogram (ECG).

IMD 16 also monitors the respiration rate of patient 14, e.g., by monitoring intrathoracic impedance, which indicative of respiration rate. As an example, intrathoracic impedance may show up as low-frequency "noise" on an unfiltered ECG signal. In different examples, IMD 16 may filter the same signals used to measure heart rate to determine respiration rate, or IMD 16 may take separate measurement to determine intrathoracic impedance. In yet another example, IMD 16 may include an intrathoracic pressure sensor or other sensor that provides an output indicative of respiration rate. It should be noted that these same techniques used to determine a respiration rate can also be used to determine that amplitude of each breath such that IMD 16 may also determine the minute ventilation of patient 14. In some instances, minute ventilation of patient 14 may be used instead of respiration rate to determine worsening heart failure in patient 14.

In the example illustrated in FIG. 1, IMD 16 includes leads 18, 20, and 22 that extend into the heart 12 of patient 14. Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. Other configurations, i.e., number and position of leads, are possible. For example, other leads or lead configurations may be used to monitor pressure and various diagnostic parameters. As described above, in some examples, IMD 16 need not be coupled to leads.

Intrathoracic impedance may be measured by creating an electrical path between electrodes (not shown in FIG. 1) located on one or more of leads 18, 20, and 22 and can electrode 34. In some embodiments, the can of IMD 16 may be used as an electrode in combination with electrodes located on leads 18, 20, and 22. For example, system 10 may measure intrathoracic impedance by creating an electrical path between RV lead 18 and electrode 34. In additional embodiments, system 10 may include an additional lead or lead segment having one or more electrodes positioned at a different location in the cardiovascular system or chest cavity, such as within one of the vena cava, subcutaneously at a location substantially opposite IMD 16 vis-à-vis the thorax of patient 14, or epicardially, for measuring intrathoracic impedance.

IMD 16 may also monitor additional diagnostic parameters in conjunction with parameters that are indicative of respiration rate, heart rate and activity level of patient 14. For example, IMD 16 may monitor atrial fibrillation burden (AF), heart rate during AF, ventricular fibrillation burden (VF), heart rate during VF, atrial tachyarrhythmia burden (AT), heart rate during AT, ventricular tachyarrhythmia burden (VT), heart rate during VT, heart rate variability, night heart rate, difference between day heart rate and night heart rate, heart rate turbulence, heart rate deceleration capacity, respiration rate, baroreflex sensitivity, percentage of cardiac resynchronization therapy (CRT) pacing, metrics of renal function, weight, blood pressure, symptoms entered by the patient via a programmer, and patient history, such as medication history, or history of heart failure hospitalizations.

IMD 16 or programmer 24 may be configured to provide an alert in response to detecting worsening heart failure in patient 14. The alert may be audible, visual, or tactile and enables patient 14 to seek medical attention to treat the condition prior to experiencing a heart failure event, or a clinician to direct patient 14 to do so. In some examples, the alert may be a silent alert transmitted to another device associated with a clinician or other user, such as a silent alert transmitted to a server, as described below, and relayed to a physician via a computing device.

In embodiments in which IMD 16 operates as a pacemaker, a cardioverter, and/or defibrillator, IMD 16 may sense electrical signals attendant to the depolarization and repolarization of heart 12 via electrodes coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

It should be understood that IMD 16 may also include other types of sensors for monitoring various diagnostic parameters. As an example, IMD 16 may monitors pressure, and one or more of leads 18, 20, and 22 and/or the device can of IMD 16 may include one or more pressure sensors, such as capacitive pressure sensors. IMD 16 may also include or be coupled to one or more pressure sensors, the output of which may be considered with heart rate to monitor baroreflex sensitivity (as well as respiration rate). In an additional example, IMD 16 may also communicate with an external sensor, such as a scale for monitoring the weight of patient 14. Moreover, in embodiments in which IMD 16 is implemented as an external device (not shown), leads for monitoring diagnostic parameters may be implanted percutaneously in patient 14 or attached to the skin of patient 14.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16. The information may relate to diagnostic parameters, i.e., information relating to activity level, heart rate, respiration rate, intrathoracic impedance, pressure, AF burden, heart rate during AF, VF burden, heart rate during VF, AT burden, heart rate during AT, VT burden, heart rate during VT, activity level, heart rate variability, night heart rate, difference between day heart rate and night heart rate, heart rate turbulence, heart rate deceleration capacity, respiration rate, baroreflex sensitivity, percentage of CRT pacing, metrics of renal function, weight, blood pressure, symptoms entered by the patient via a programmer, and patient history, such as medication history, or history of heart failure hospitalizations. The information may also include trends therein over time. In some embodiments, the user may use programmer 24 to retrieve information from IMD 16 regarding other sensed physiological parameters of patient 14. In addition, the user may use programmer 24 to retrieve information from IMD 16 regarding the performance or integrity of IMD 16 or other components of system 10, such as leads 18, 20, and 22, or a power source of IMD 16.

In one example, a user may also use programmer 24 to program other parameters related to detecting worsening heart failure, such as parameters associated with the predetermined threshold zone (e.g., as shown in FIGS. 7A-7D) for a given patient activity level. In this case, the user may specify parameters that define the predetermined threshold zone for a given patient activity level, or parameters that control how the predetermined threshold zone for a given patient activity level changes over time. Furthermore, the user may use programmer 24 to enter clinical information, such as patient history, medication history, history of heart failure hospitalizations, or other historical or current observations of patient condition.

Programmer 24 may also be used to program a therapy progression, select electrodes to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
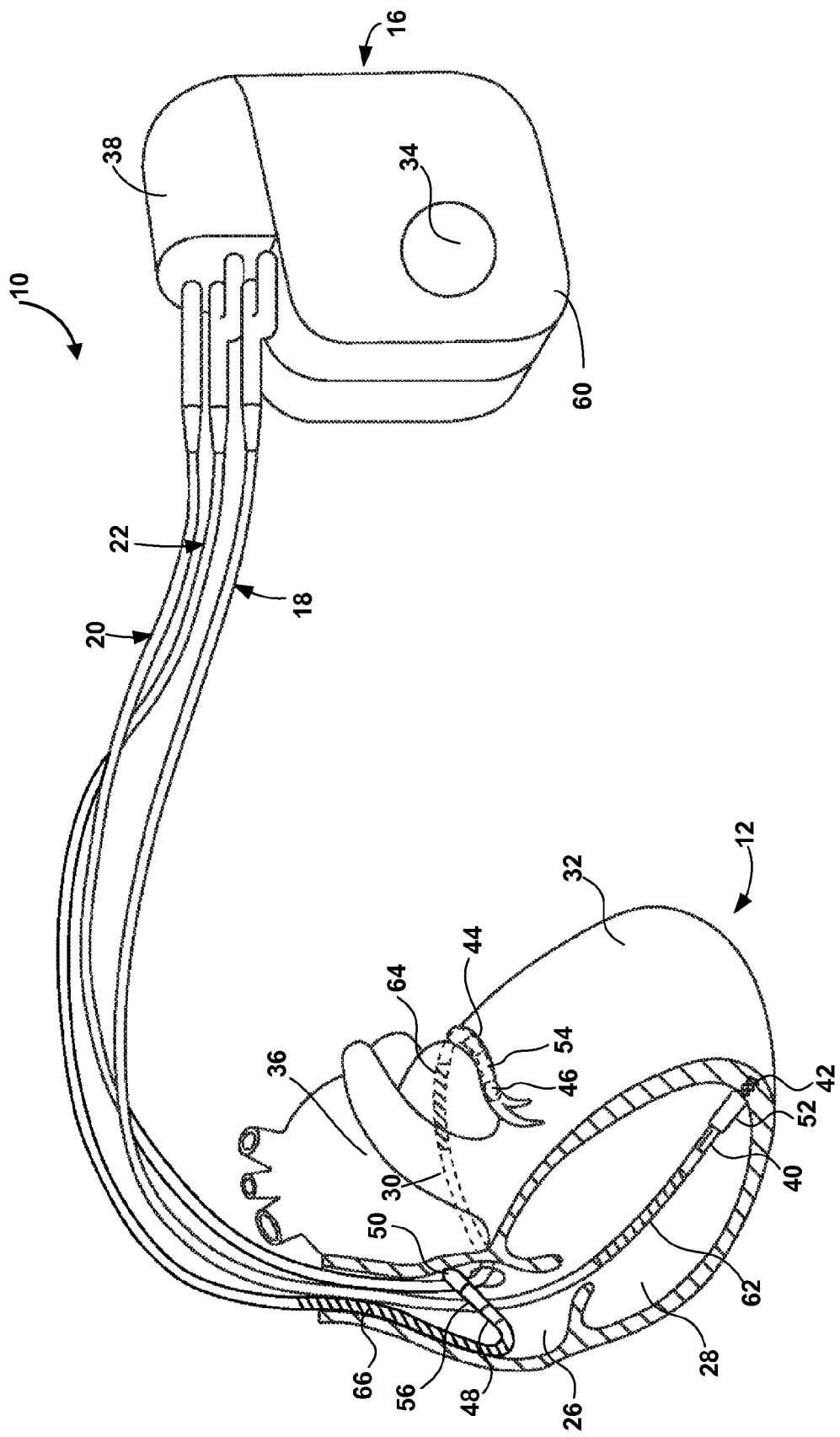
FIG. 2 is a conceptual diagram illustrating the implantable medical device (IMD) and leads of the system shown in FIG. 1 in greater detail.

FIG. 2 is a conceptual diagram illustrating IMD 16, leads 18, 20, and 22, and electrode 34 of system 10 in greater detail. System 10 is generally described in this disclosure as a therapy system that detects worsening heart failure in patient 14 and delivers corrective electrical signals to heart 12. In particular, system 10 is as a therapy system that monitors parameters that are indicative of respiration rate, heart rate and activity level to detect worsening heart failure in patient 14.

In the example illustrated in FIG. 2, system 10 includes leads 18, 20, and 22 that include electrodes for monitoring parameters that are indicative of respiration rate and heart rate and. Leads 18, 20, and 22 may be electrically coupled to a stimulation generator and a sensing module of IMD 16 via connector block 38. In some examples, proximal ends of leads 18, 20, 22 may include electrical contacts that electrically couple to respective electrical contacts within connector block 38. In addition, in some examples, leads 18, 20, 22 may be mechanically coupled to connector block 38 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In some cases, each of the leads 18, 20, 22 may include cable conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

As discussed above, IMD 16 includes one or more housing electrodes, such as housing electrode 34, which may be formed integrally with an outer surface of hermetically-sealed housing 60 of IMD 16 or otherwise coupled to housing 60. In some examples, housing electrode 34 is defined by an uninsulated portion of an outward facing portion of housing 60 of IMD 16. Other division between insulated and uninsulated portions of housing 60 may be employed to define two or more housing electrodes. In some examples, housing electrode 34 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 34, 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 34. Additionally, any of the electrodes 40, 42, 44, 46, 48, 50, 62, 64 and 66 may be used in combination with housing electrode 34 to sense intrathoracic impedance of patient 14.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 34 in a unipolar configuration. Furthermore, IMD 16 may deliver cardioversion or defibrillation pulses to heart 12 via any combination of elongated electrodes 62, 64, 66, and housing electrode 34. Electrodes 34, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Moreover, IMD 16 need not be implanted within patient 14 as shown in FIG. 1. For example, IMD 16 may be implanted subcutaneously in patient 14 or may be located outside the body of patient 14. In such examples, IMD 16 may monitor diagnostic parameters and deliver defibrillation pulses and other therapies to heart 12 via percutaneous leads that extend through the skin of patient 14 to a variety of positions within or outside of heart 12.

In addition, in other examples, system 10 may include any suitable number of leads coupled to IMD 16, and each of the leads may extend to any location within or proximate to heart 12 or in the chest of patient 14. For example, other example therapy systems may include three transvenous leads and an additional lead located within or proximate to left atrium 36. As other examples, a therapy system may include a single lead that extends from IMD 16 into right atrium 26 or right ventricle 28, or two leads that extend into a respective one of the right ventricle 28 and right atrium 26.

Figure 3:
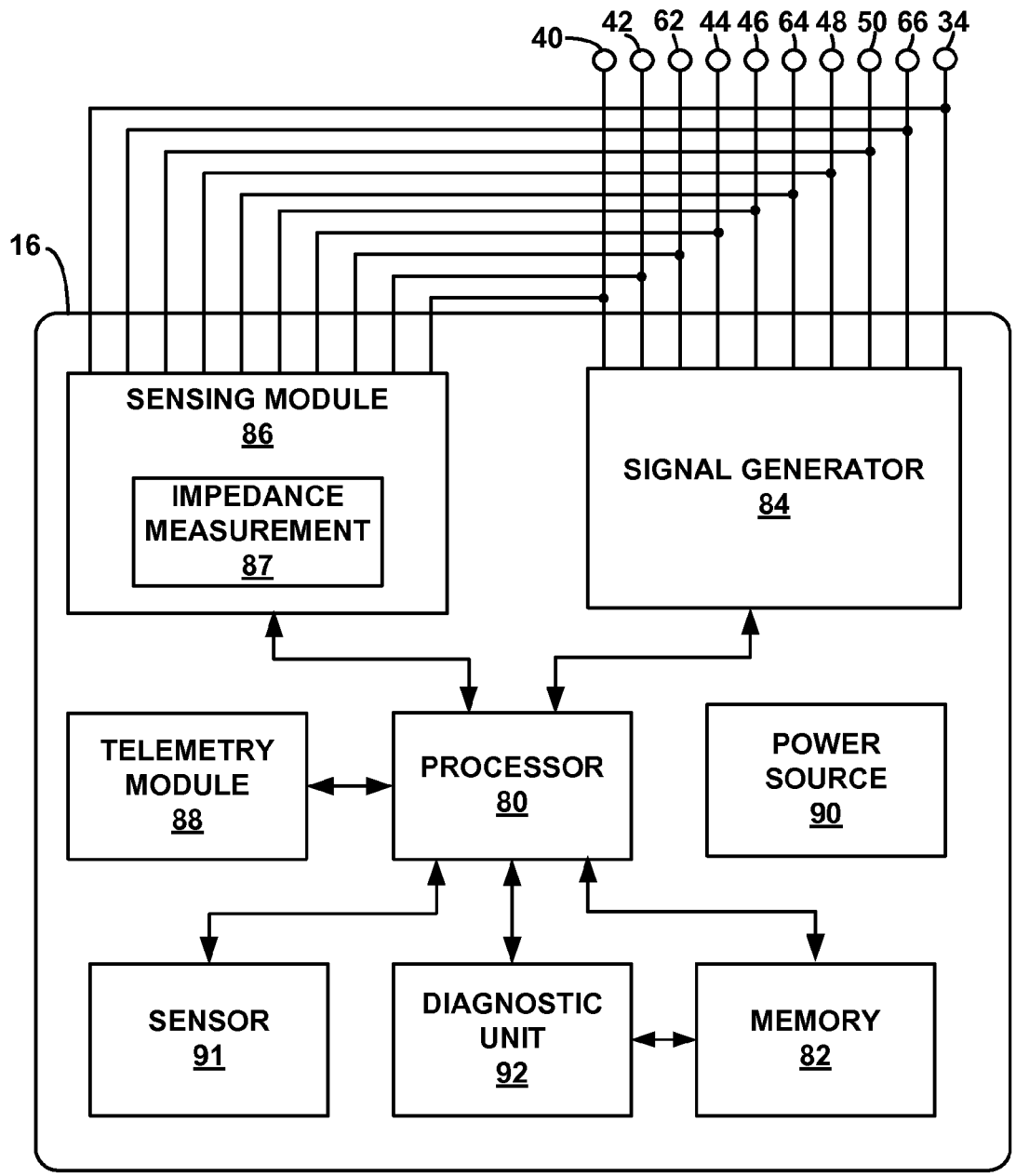
FIG. 3 is a functional block illustrating an example configuration of the IMD shown in FIG. 1.

FIG. 3 is a functional block diagram of one example of IMD 16, which includes a processor 80, memory 82, signal generator 84, electrical sensing module 86, telemetry module 88, power source 90, sensor 91 and diagnostic unit 92. Processor 80 may comprise one or more processors. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

IMD 16 includes sensor 91 generates an output based on activity level of patient 14. In exemplary embodiments, sensor 91 is a 3-axis accelerometer, such as a piezoelectric and/or micro-electro-mechanical accelerometer. In other embodiments, a single axis accelerometer may be employed, or multiple single axis accelerometers may be used in place of one 3-axis accelerometer.

In some embodiments, processor 80 processes the analog output of sensor 91 to determine digital activity information. For example, where sensor 91 comprises a piezoelectric accelerometer, processor 80 may process the raw signal provided by sensor 91 to determine activity counts. In some embodiments, IMD 16 includes multiple sensors oriented along various axes, or sensor 91 comprises a single multi-axis, e.g., three-axis, accelerometer. In such embodiments, processor 80 may process the signals provided by the one or more sensor 91 to determine velocity of motion information for each axis.

Figure 6:
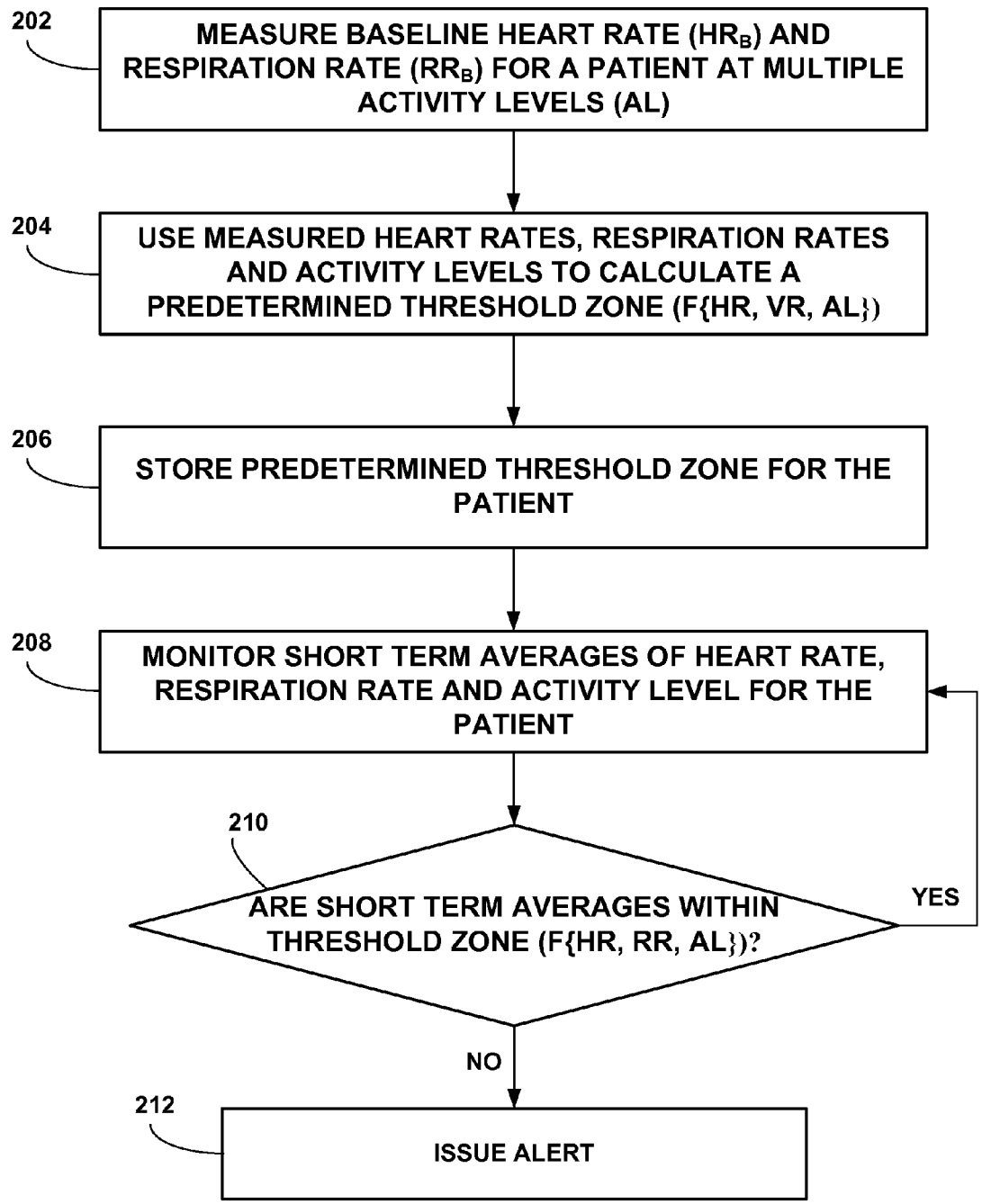
FIG. 6 is a flow diagram illustrating an example method to detect worsening heart failure in a patient using a predetermined threshold zone for the patient.

Sensor 91 may comprise one or more sensors. Sensor 91 is shown in FIG. 6 as being housed within a housing (not shown) of IMD 16. However, in some embodiments, at least one sensor 91 is coupled to IMD 16 via additional leads (not shown). Such sensors may be located anywhere within patient 14. In some embodiments, IMD 16 may be coupled to multiple accelerometers located at various positions within patient 14 or on the external surface of patient 14, and processor 80 may receive more detailed information about the posture of and activity undertaken by patient 14. For example, accelerometer sensor 91 may be located within the torso and at a position within a limb, e.g. a leg, of patient 14.

In some embodiments, one or more sensor 91 may communicate wirelessly with IMD 16 instead of requiring a lead to communicate with the IMD. For example, a sensor located external to patient 12 may communicate wirelessly with processor 80, either directly or via programmer 24. In some embodiments, one or more sensor 91 may be included as part of or coupled to programmer 24.

Moreover, the invention is not limited to embodiments where sensor 91 includes one or more accelerometers. In some embodiments, one or more sensor 91 may take the form of, for example, a thermistor, a pressure transducer, or electrodes to detect thoracic impedance or an electrogram. Such sensors may be appropriately positioned within patient 14, or on an external surface of the patient, to allow processor 80 to measure a physiological parameter of patient 14, such as a skin temperature, an arterial or intracardiac pressure, a respiration rate, a heart rate, or a Q-T interval of patient 14.

As illustrated in FIG. 3, sensing module 86 may include an impedance measurement module 87. Processor 80 may control impedance measurement module 87 to periodically measure an electrical parameter to determine an impedance, such as an intrathoracic impedance. For an intrathoracic impedance measurement, processor 80 may control stimulation generator 84 to deliver an electrical signal between selected electrodes and impedance measurement module 87 to measure a current or voltage amplitude of the signal. Processor 80 may select any combination of electrodes 34, 40, 42, 44, 46, 48, 50, 62, 64, and 66, e.g., by using switch modules in signal generator 84 and sensing module 86. Impedance measurement module 87 includes sample and hold circuitry or other suitable circuitry for measuring resulting current and/or voltage amplitudes. Processor 80 determines an impedance value from the amplitude value(s) received from impedance measurement module 87.

In some examples, processor 80 may perform an impedance measurement by causing signal generator 84 to deliver a voltage pulse between two electrodes and examining resulting current amplitude value measured by impedance measurement module 87. In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12.

In other examples, processor 80 may perform an impedance measurement by causing signal generator 84 to deliver a current pulse across two selected electrodes. Impedance measurement module 87 holds a measured voltage amplitude value. Processor 80 determines an impedance value based upon the amplitude of the current pulse and the amplitude of the resulting voltage that is measured by impedance measurement module 87. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may measure intrathoracic impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

Electrical sensing module 86 monitors signals from at least one of electrodes 34, 40, 42, 44, 46, 48, 50, 62, 64 or 66 in order to monitor electrical activity of heart 12. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is hereby incorporated by reference in its entirety. Other amplifiers may also be used. Furthermore, in some examples, one or more of the sensing channels of sensing module 84 may be selectively coupled to housing electrode 34, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

In the illustrated example shown in FIG. 3, IMD 16 includes diagnostic unit 92. Diagnostic unit 92 provides functionality that enables IMD 16 to detect worsening heart failure in patient 14. To avoid confusion, although diagnostic unit 92 is described as performing the various monitoring and detecting techniques proscribed to IMD 16, it should be understood that these techniques may also be performed by processor 80, e.g., that diagnostic unit 92 may be a functional module provided or executed by processor 80. Accordingly, although processor 80 and diagnostic unit 92 are illustrated as separate modules in FIG. 3, processor 80 and diagnostic unit 92 may be incorporated in a single processing unit or equivalent circuitry.

In operation, diagnostic unit 92 monitors respiration rate, one or more parameters that are indicative of heart rate and one or more parameters that are indicative of an activity level of patient 14 to detect worsening heart failure in patient 14. Diagnostic unit 92 detects worsening heart failure in patient 14 by comparing respiration rate and heart rate to predetermined levels associated with patient 14 for a given activity level.

In the example illustrated in FIG. 3, diagnostic unit 92 may receive signals or indications from processor 80, sensing module 86 or other sensors 91 to diagnostic parameters. Thus, IMD 16 may be configured to monitor any physiological parameters that are capable of being sensed using any combination of electrodes 34, 40, 42, 44, 46, 48, 50, 62, 64 and 66 in addition to those indicative of respiration rate and heart rate. For example, IMD 16 may be configured to monitor intrathoracic impedance and/or electrical activity of heart 12, using any combination of electrodes 34, 40, 42, 44, 46, 48, 50, 62, 64 and 66.

Based on the electrical activity of heart 12 as indicated by sensing module 86, diagnostic unit 92 may monitor AF burden, heart rate during AF, VF burden, heart rate during VF, AT burden, heart rate during AT, VT burden, heart rate during VT, heart rate variability, night heart rate difference between day heart rate and night heart rate, heart rate turbulence, heart rate deceleration capacity, or baroreflex sensitivity. As previously described, sensing module 86 monitors signals from a selected combination of electrodes 34, 40, 42, 44, 46, 48, 50, 62, 64, and 66 and processor 80/diagnostic unit 92 may detect atrial or ventricular tachyarrhythmia based on signals or indications from sensing module 86. An AT burden may be determined based on the number and/or duration (individual, average, or collective) of incidents of AT, as well as the ventricular rate during AT. AF, VT and VF burdens may be similar determined. In some examples, AT and AF burdens are combined as an AT/AF burden. VT and VF burdens may likewise be combined, in some examples.

Processor 80 controls signal generator 84 to deliver stimulation therapy to heart 12 based on a selected one or more of therapy programs, which may be stored in memory 82. Specifically, processor 80 may control signal generator 84 to deliver electrical pulses with the amplitudes, pulse widths, frequency, or electrode polarities specified by the selected one or more therapy programs.

Signal generator 84 is electrically coupled to electrodes 34, 40, 42, 44, 46, 48, 50, 62, 64, and 66, e.g., via conductors of the respective lead 18, 20, 22, or, in the case of housing electrode 34, via an electrical conductor disposed within housing 60 of IMD 16. A switch matrix may also be provided to connect signal generator 84 to one or more of electrodes 34, 40, 42, 44, 46, 48, 50, 62, 64, and 66. Signal generator 84 is configured to generate and deliver electrical stimulation therapy to heart 12.

For example, signal generator 84 may deliver defibrillation shocks to heart 12 via at least two of electrodes 34, 62, 64, 66. Signal generator 84 may also deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, transistor array, microelectromechanical switches, or any other type of switching device suitable to selectively couple stimulation energy to selected electrodes.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" indicates dual chamber, "V" may indicate a ventricle, "I" indicates inhibited pacing (e.g., no pacing), and "A" indicates an atrium. The first letter in the pacing mode indicates the chamber that is paced, the second letter indicates the chamber that is sensed, and the third letter indicates the pacemaker response to sensing. In addition, "R" indicatives that the therapy is rate-responsive.

Intervals defined by the pacer timing and control module within processor 80 may include atrial and ventricular pacing escape intervals, refractory periods during which sensed P-waves and R-waves are ineffective to restart timing of the escape intervals, the pulse widths of the pacing pulses, A-V intervals, and V-V intervals for cardiac resynchronization therapy (CRT). As another example, the pacer timing and control module may define a blanking period, and provide signals sensing module 86 to blank one or more channels, e.g., amplifiers, for a period during and after delivery of electrical stimulation to heart 12. As another example, the pacer timing and control module may control intervals for delivery of refractory period stimulation or cardiac potentiation therapy. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 34, 40, 42, 44, 46, 48, 50, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing (ATP).

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as an atrial or ventricular fibrillation or tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are hereby incorporated by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, signal generator 84 may include a high voltage charge circuit and a high voltage output circuit. If IMD 16 is configured to generate and deliver pacing pulses to heart 12, signal generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of signal generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 34 serves as cathode or anode, and which electrodes are involved in delivery of the cardioversion or defibrillation pulses. Such functionality may be provided by one or more switches or a switching module of signal generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is hereby incorporated by reference in its entirety.

IMD 16 may also be configured, in various examples, to monitor other diagnostic parameters. In some examples, diagnostic unit 92 may receive signals or information from external sources, such as programmer 24 or an external sensor, such as a scale, and monitor such information or signals. Additionally, diagnostic unit 92 may receive information from processor 80, or may maintain information in memory 82, indicating percentage of CRT pacing. Diagnostic unit 92 or processor 80 may determine whether or not CRT pacing is delivered based on information from processor 80 of a pacer timing and control module thereof.

If diagnostic unit 92 detects worsening heart failure of patient 14, diagnostic unit 92 may provide an alert to patient 14. Diagnostic unit 92 may include or be coupled to an alert module (not shown) that provides, as examples, an audible or tactile alert to patient 14 of the worsening heart failure. In some examples, diagnostic unit 92 additionally or alternatively provide an indication of worsening heart failure to programmer 24 or another device via telemetry module 88 and/or network, which may provide an alert to a user, such as patient 14 or a clinician.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 4:
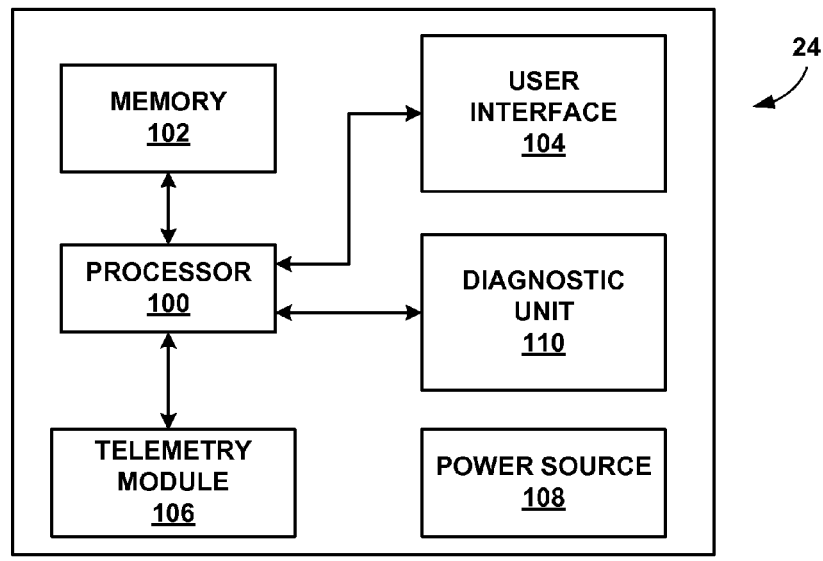
FIG. 4 is a functional block diagram illustrating an example configuration of the programmer shown in FIG. 1.

FIG. 4 is block diagram of an example programmer 24. As shown in FIG. 4, programmer 24 includes processor 100, memory 102, user interface 104, telemetry module 106, and power source 108. In some examples, programmer 24, as illustrated in FIG. 4, includes a diagnostic unit 110. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select predetermined threshold zone for a given patient activity level characteristics, and select rules for detecting worsening heart failure in patient 14 based on the selected diagnostic parameters and predetermined threshold zone for a given patient activity level. A user may also use programmer 24 to configure other sensing or any therapy provided by IMD 16. The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Diagnostic unit 110, although illustrated as a separate module in FIG. 4, may be incorporated in a single processing unit with processor 100 or functional module executed or provided by processor 100. Memory 102 may store instructions that cause processor 100 and/or diagnostic unit 110 to provide the functionality ascribed to programmer 24 herein, and information used by processor 100 and/or diagnostic unit 110 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls operation of IMD 16, such as therapy delivery values.

A user, such as a clinician, technician, or patient 14, may interact with programmer 24 via user interface 104. User interface 106 may include display to present graphical user interface to a user, and a keypad or another mechanism for receiving input from a user. In some examples, user interface 106 may include a touch screen display.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 3).

Programmer 24 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In some examples, IMD 16 may detect worsening heart failure using any of the techniques described herein, and provide an indication of worsening heart failure to programmer 24. In such examples, programmer 24 need not include diagnostic module 110. Processor 100 may control user interface 106 to provide an alert of worsening heart failure of patient 14 to the patient, a clinician, or other users. In some examples, processor 100 may provide an alert of worsening heart failure of patient 14 to one or more computing devices via a network. A user may use programmer 24 to retrieve and/or view data regarding diagnostic parameters.

In some examples, programmer 24 includes diagnostic module 110 that receives diagnostic data from IMD 16, or other implanted or external sensors or devices, i.e., data regarding diagnostic parameters, and processes the received data to detect worsening heart failure in patient 14. In this manner, diagnostic unit 110 may perform substantially the same functionality as described with respect to diagnostic unit 92 in FIG. 3. IMD 16 may not need to include diagnostic unit 92 in examples in which programmer 24 includes diagnostic unit 110. Diagnostic unit 110 may include an alert module that provides an alert to patient 14 or a clinician via user interface 104 when worsening heart failure is detected in patient 14, and/or provides a notification to one or more computing devices via a network.

Alerts provided via user interface 104 may include a silent, audible, visual, or tactile alert. For example, user interface 104 may emit a beeping sound, display a text prompt, cause various buttons or screens to flash, or vibrate to alert patient 14 or another user that a heart failure decompensation event may be likely to occur. Patient 14 may then seek medical attention, e.g., check in to a hospital or clinic, to receive appropriate treatment, or the other user may instruct patient 14 to do so.

Although illustrated and described in the context of examples in which programmer 24 is able to program the functionality of IMD 16, in other examples a device capable of communicating with IMD 16 and providing functionality attributed to programmer 24 herein need not be capable of programming the functionality of the IMD. For example, an external home or patient monitor may communicate with IMD 16 for any of the purposes described herein, but need not independently be capable of programming the functionality of the IMD. Such as a device may be capable of communicating with other computing devices via a network, as discussed in greater detail below.

The components of and functionality provided by a diagnostic unit for detecting worsening heart failure are described in greater detail below with respect to diagnostic unit 92 of IMD 16. However, it is understood that any diagnostic unit provided in any device, such as diagnostic unit 110 of programmer 24, may include the same or similar components and provide the same or similar functionality.

Figure 5:
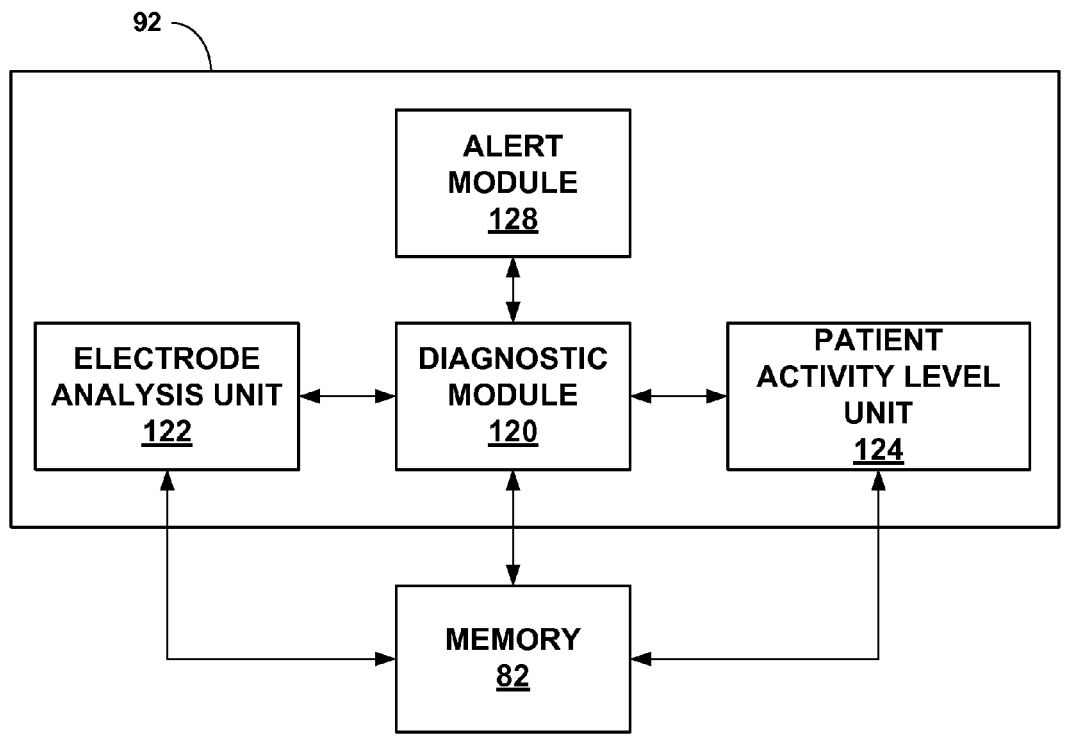
FIG. 5 is a functional block diagram illustrating an example configuration of the diagnostic units shown in FIG. 3 and FIG. 4.

FIG. 5 is a block diagram of an example configuration of diagnostic unit 92. As shown in FIG. 5, diagnostic unit 92 includes multiple components including diagnostic module 120, electrode analysis unit 122, and patient activity level unit 124, and alert module 128. Because either IMD 16 or programmer 24 may be configured to include a diagnostic unit, modules 120, 122, 124, and 128 (and their sub-modules described below with reference to FIGS. 6-8) may be implemented in one or more processors, such as processor 80 of IMD 16 or processor 100 of programmer 24. The modules of diagnostic unit 92 (and their sub-modules described below with reference to FIGS. 6-8) may be embodied as one or more hardware modules, software modules, firmware modules, or any combination thereof.

Generally, diagnostic module 120 processes data received from electrode analysis unit 122 and patient activity level unit 124 to detect worsening heart failure in patient 14. Accordingly, electrode analysis unit 122 and patient activity level unit 124 may operate in a coordinated manner with diagnostic module 120. In one example embodiment, diagnostic module 120 may retrieve timing information from memory 126. The timing information may provide periodic intervals for monitoring a heart rate, a respiration rate and an activity level of a patient and detecting worsening heart failure based on the parameters. Accordingly, diagnostic module 120 may invoke electrode analysis unit 122 and patient activity level unit 124 based on the timing information. Alternatively, diagnostic module 120 may load the timing information into electrode analysis unit 122 and patient activity level unit 124, and units 122 and 124 may monitor corresponding parameters according to the timing information.

Electrode analysis unit 122 monitors the intrathoracic impedance of patient 14 as previously described to monitor heart rate and respiration rate. That is, electrode analysis unit 122 may receive signals indicative of to monitor heart rate respiration rate, e.g., ECG information and/or intrathoracic impedance values. Although electrode analysis unit 122 is illustrated in FIG. 5, it should be understood that electrode analysis unit 122 is one example of a diagnostic parameter analysis units that may be utilized to monitor heart rate and respiration rate. In other example embodiments, diagnostic unit 92 may be configured to include, a pressure analysis unit that monitors one or more intrathoracic or cardiovascular pressures of patient 14.

Patient activity level unit 124 monitors a patient activity level. As an example, patient activity level unit 124 may receive an input from one or more sensors, including, e.g., a 3-axis accelerometer, such as a piezoelectric and/or micro-electro-mechanical accelerometer that generates an output based on activity level.

Diagnostic module 120 processes data received from electrode analysis unit 122 and patient activity level unit 124 and compares the received data to a predetermined threshold zone that corresponds to baseline heart rates and respiration rates for a given activity level of a patient. Memory 82 may store an indication of predetermined threshold zone for a patient.

Diagnostic module 120 invokes alert module 128 in response to detecting worsening heart failure in patient 14. Alert module 128 provides an alert to patient 14 by, for example, providing an audible, visual, or tactile alert. Alert module 128 may cause IMD 16 to emit a beeping a sound or vibrate. In some examples, alert module 128 may provide an alert by communicating with an external device, such as programmer 24. In response to the communication from alert module 128, programmer 24 may emit a beeping sound, display a text prompt, vibrate, or cause buttons and/or screens of programmer 24 to flash. Similarly, if the alert module is implemented in programmer 24, alert module 128 may cause programmer 24 to send a telemetry signal to IMD 16 that causes IMD 16 to generate the alert.

In some examples, electrode analysis unit 122 may determine a current impedance value, a reference impedance value and fluid index value using any of the techniques described in a commonly-assigned commonly-assigned U.S. application Ser. No. 10/727,008 by Stadler et al., published as U.S. Patent Publication No. 2004/0172080 and entitled "METHOD AND APPARATUS FOR DETECTING CHANGE IN INTRATHORACIC IMPEDANCE," filed on Dec. 3, 2003, which is hereby incorporated by reference in its entirety.

FIG. 6 is a flow diagram illustrating an example method to detect worsening heart failure in a patient using a predetermined threshold zone for the patient. For clarity, the techniques shown in FIG. 6 are discussed with respect to system 10 (FIGS. 1-5) and patient 14 (FIG. 1).

The techniques shown in FIG. 6 necessitate establishing a predetermined threshold zone corresponding to a baseline heart rate ($HR_B$) and baseline respiration rate ($RR_B$) at multiple activity levels (AL) for patient 14. In the example shown in FIG. 6, a clinician measures baseline heart rates and baseline respiration rates at a multitude of activity levels of patient 14 (202). Importantly, patient 14 should not be experiencing decompensation when the clinician measures the baseline heart rates and baseline respiration rates.

As one example, the clinician may measure a patient's baseline heart rates and baseline respiration rates in a controlled setting for multiple activity levels. Examples of different activity levels include sleeping, resting (e.g., reading or watching television), daily activity (e.g., walking or cooking) and high (consistent with exercise). The patient's activity level may be quantified in the controlled environment. As a further example, IMD 16 may record a series of data points representing measured heart rates, respiration rates and activity levels for over an initial programming period. For example, a clinician may program IMD 16 to record the series of data points representing measured heart rates, respiration rates and activity levels in an initial patient visit. In such an example, IMD 16 may record the measured heart rates, respiration rates and activity levels for a predetermined amount of time (e.g., 24 hours, 1 week, 1 month), until a suitable number of data points are recorded for each activity level or until a subsequent patient visit.

After measuring heart rates, respiration rates and activity levels of patient 14, the measured heart rates, respiration rates and activity levels of patient 14 are used to define a predetermined threshold zone (TZ) which is a function of heart rate, respiration rate and activity level (204). As shown in Equation 1, the predetermined threshold zone can be represented as a function of heart rates, respiration rates and activity level.

TZ=F{$HR_B$,$RR_B$,AL}     Equation 1

As discussed in greater detail with respect to FIGS. 7A-7D, the predetermined threshold zone can be graphically represented as a continuous area within a three-dimensional space including dimensions representing heart rate, respiration rates and activity level of patient 14.

Once calculated, the IMD 16 and/or programmer 24 store the predetermined threshold zone in memory (206). Once the predetermined threshold zone is stored in memory, system 10 is ready to begin monitoring patient 14 for worsening heart failure. As examples, after reviewing or imputing the predetermined threshold zone stored in memory of system 10, the clinician may program IMD 16 to begin monitoring the heart rate, respiration rate and activity level of patient 14 (208) and comparing the monitored heart rate, respiration rate and activity level to the threshold zone (210). In order to prevent false alerts, IMD 16 may average a series of measurements of heart rate, respiration rate and activity level and compare the average heart rate, respiration rate and activity levels of the patient to the predetermined threshold zone. As examples, system 10 may average the heart rate, respiration rate and activity level of patient 14 measurements taken over a period of between five seconds and five minutes for comparison to the predetermined threshold zone. For example, 10 may average the heart rate, respiration rate and activity level of patient 14 measurements taken over a period of fifteen seconds, thirty seconds, one minute or two minutes for comparison to the predetermined threshold zone. System 10 continues to monitor heart rate, respiration rate and activity level unless and until one or more measurements are outside of the predetermined threshold zone.

In the event that, one or more measurements heart rate, respiration rate and activity level of patient 14 are outside of the predetermined threshold zone for patient 14 either IMD 16 or programmer 24 issues an alert to patient 14 (212). The alert may be audible, visual, or tactile and enables patient 14 to seek medical attention to treat the condition prior to experiencing a heart failure event, or a clinician to direct patient 14 to do so. In some examples, the alert may be a silent alert transmitted to another device associated with a clinician or other user, such as a silent alert transmitted to a server, as described below, and relayed to a physician via a computing device. In some examples, system 10 may continue to monitor heart rate, respiration rate and activity level even after issuing an alert.

In addition, in some examples system 10 may store monitored heart rate, respiration rate and activity level information. For example, system 10 may store the most recent monitored heart rate, respiration rate and activity level information, e.g., the most recent day, week or month of information depending on the amount of memory allocated to store monitored heart rate, respiration rate and activity level information. As another example, system 10 may store monitored heart rate, respiration rate and activity level information within a defined time period before and after determining that the heart rate, respiration rate and activity level unless are outside of the predetermined threshold zone.

Figure 7A:
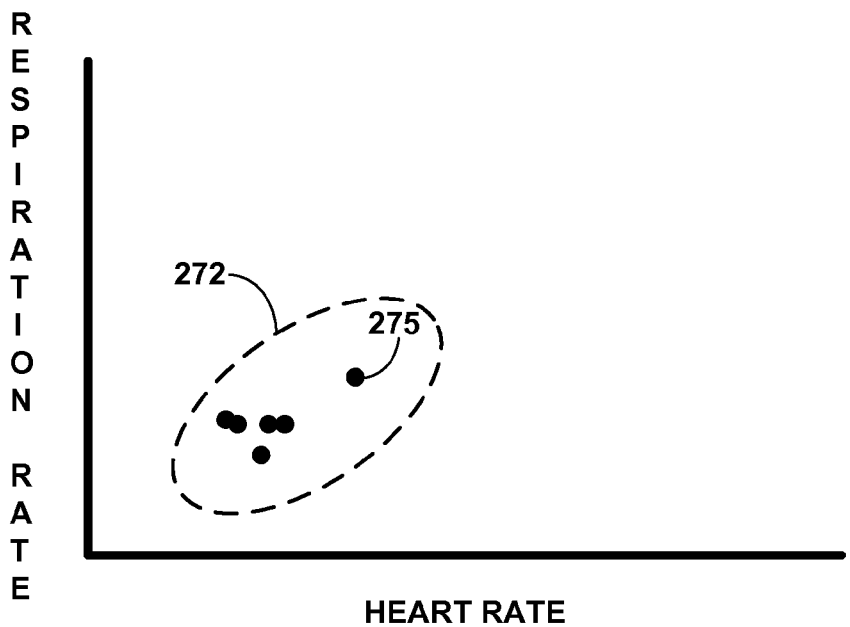
FIGS. 7A-7D are graphical representations of an example predetermined threshold zone at different activity levels of a patient.
Figure 7B:
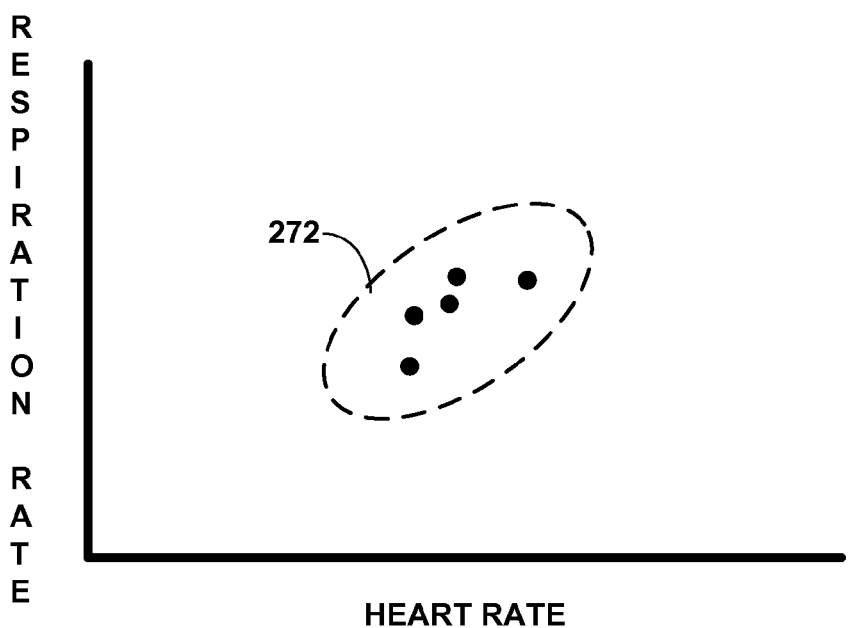
Figure 7C:
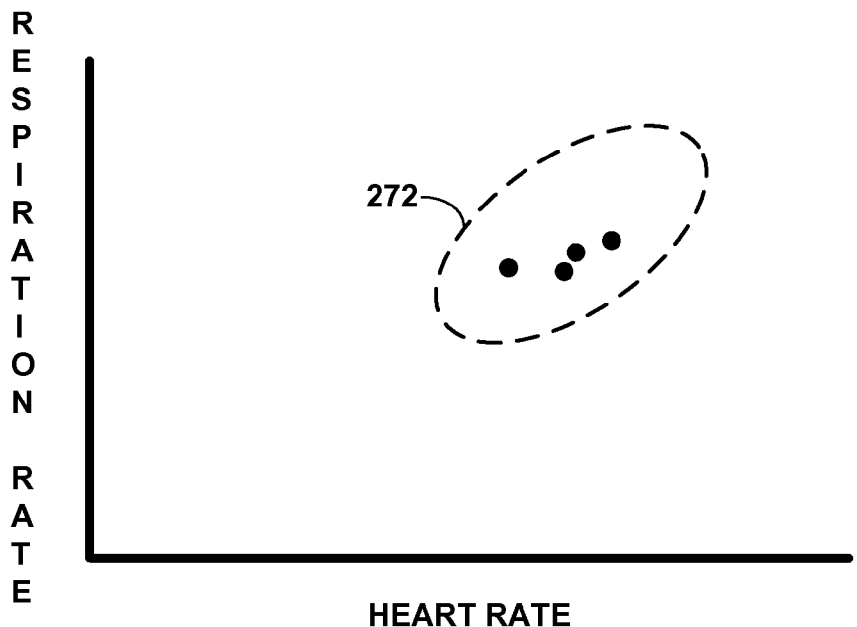
Figure 7D:
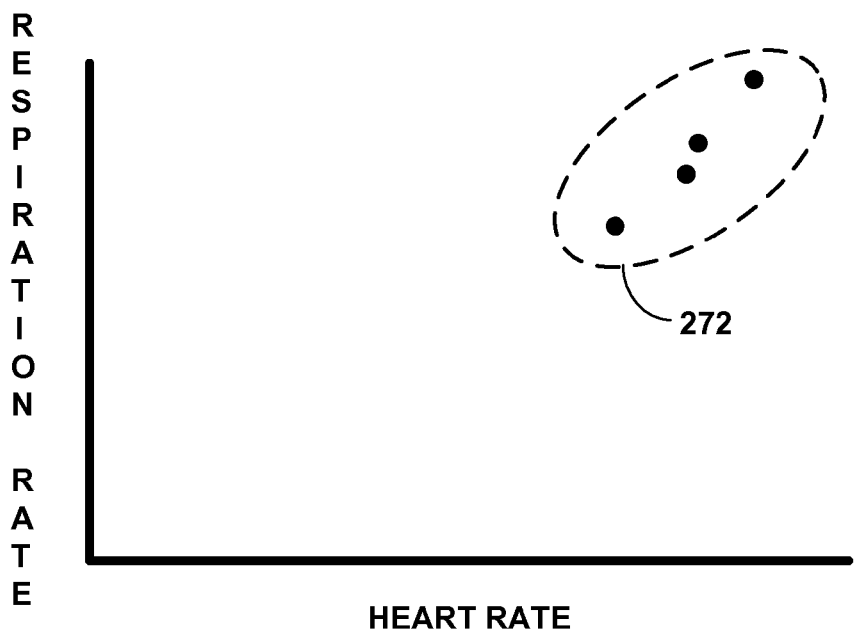

FIGS. 7A-7D are graphical representations of exemplary predetermined threshold zone 272 at different activity levels of a patient. Specifically, FIG. 7A illustrates predetermined threshold zone 272 at a sleeping activity level; FIG. 7B illustrates predetermined threshold zone 272 at a resting (e.g., reading or watching television) activity level; FIG. 7C illustrates predetermined threshold zone 272 at a daily activity (e.g., walking or cooking) activity level; FIG. 7D illustrates predetermined threshold zone 272 at a and high (consistent with exercise) activity level. While FIGS. 7A-7D represent predetermined threshold zone 272 at discrete activity levels, predetermined threshold zone 272 may be considered to be a continuous zone including any activity level. For example, predetermined threshold zone 272 could be graphically represented as a continuous area within a three-dimensional space including dimensions representing heart rate, respiration rates and activity level. As represented in FIGS. 7A-7D, according to predetermined threshold zone 272, a higher activity level corresponds to higher respiration rates and heart rates for the patient.

FIGS. 7A-7D also illustrate a series of data points representing baseline heart rates and respiration rates for a patient for each activity level. A representative data point in the series is indicated by reference numeral 275 in FIG. 7A. As an example, the series of data points shown in FIGS. 7A-7D could be produced as described with respect to FIG. 6 and step 202. The series of data points shown in FIGS. 7A-7D can be used to calculate predetermined threshold zone 272.

In different examples, either IMD 16, programmer 24 or an external device can be used to calculate the predetermined threshold zone 272. Generally, a predetermined threshold zone includes a majority of the data points in the series of data points. For example, the predetermined threshold zone for a patient may include a substantially all of the data points in the series of data points. In addition, the predetermined threshold zone may extend beyond the majority of the data points in the series of data points. As an example, the series of data points may be used as a data set to define the predetermined threshold zone using statistical analysis. As one example, the predetermined threshold zone may extend to 1, 2 or 3 standard deviations from the data points in the series of data points. As another example, the predetermined threshold zone may include any area in which heart rate and/or respiration rate is actually lower than the majority of the data points in the series of data points for a given activity level of patient 14 as lower heart rate and/or respiration rate for a given activity level would not generally indicate worsening cardiac condition of patient 14. In addition, the predetermined threshold zone may extend only a limited amount beyond the majority of the data points in the series of data points for a given activity level of patient 14. For example, because a higher heart rate and/or respiration rate for a given activity level is an indication of worsening cardiac condition of patient 14, the upper limits of heart rate and respiration rate dimensions of the predetermined threshold zone may be limited.

It should be noted that any suitable technique may be used to calculate the predetermined threshold zone for a patient. As an example, additional factors, including but not limited to patient medical history, family history, age, height, weight, body mass index, gender and race may also be used as inputs to calculate a predetermined threshold zone specifically for a patient.

Figure 8:
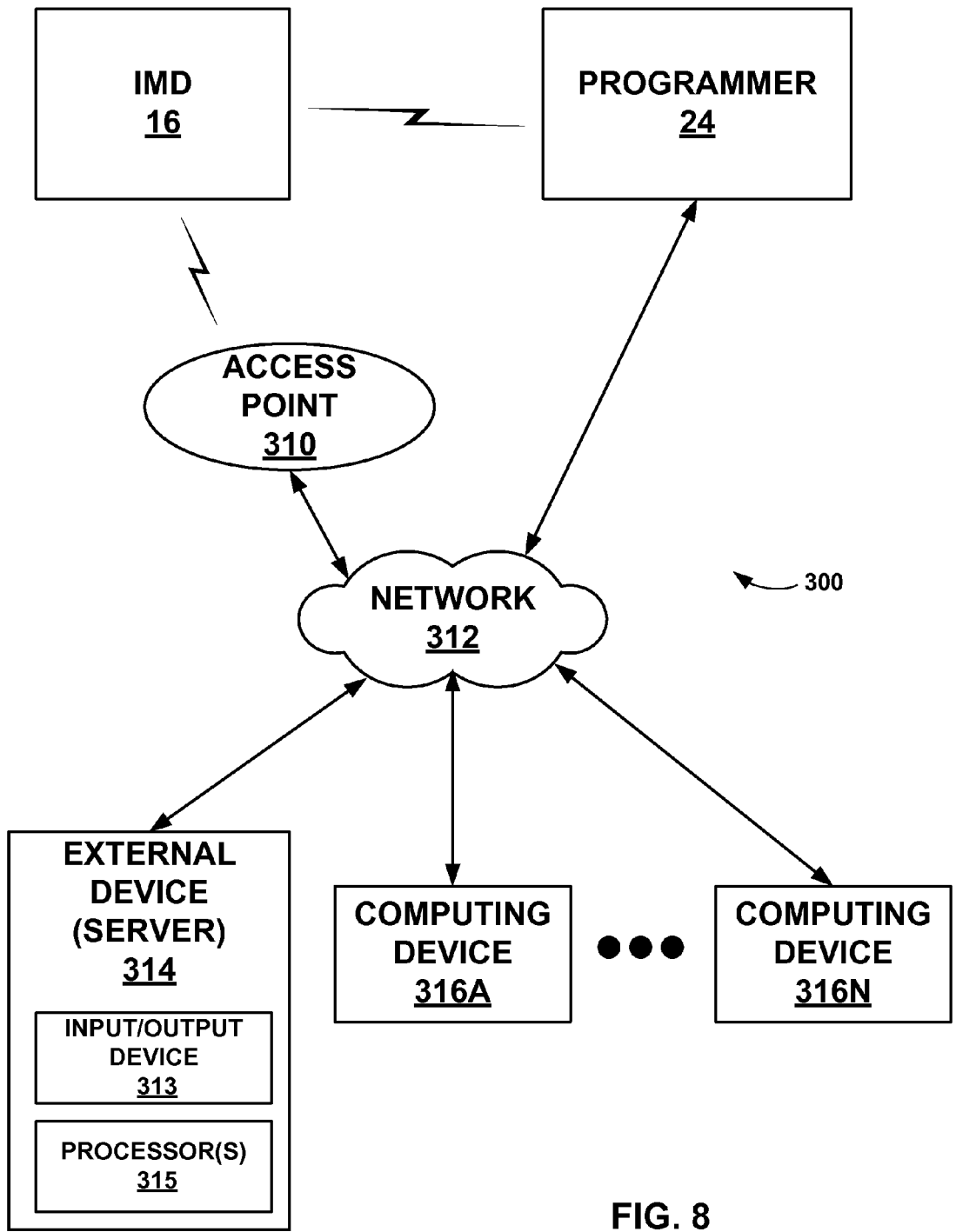
FIG. 8 is a block diagram illustrating an example system that includes an external device, such as a server, and one or more computing devices that are coupled to the IMD and programmer shown in FIG. 1 via a network.

FIG. 8 is a block diagram illustrating an example system 300 that includes an external device, such as a server 314, and one or more computing devices 316A-316N ("computing devices 316") that are coupled to IMD 16 and programmer 24 shown in FIG. 1 via a network 312. In this example, IMD 16 may use its telemetry module 88 to communicate with programmer 24 via a first wireless connection, and to communication with an access point 310 via a second wireless connection. In the example of FIG. 8, access point 310, programmer 24, server 314, and computing devices 316A-216N are interconnected, and able to communicate with each other, through network 312. In some cases, one or more of access point 310, programmer 24, server 314, and computing devices 316A-316N may be coupled to network 312 through one or more wireless connections. IMD 16, programmer 24, server 314, and computing devices 316A-216N may each comprise one or more processors, such as one or more microprocessors, DSPs, ASICs, FPGAs, programmable logic circuitry, or the like, that may perform various functions and operations, such as those described herein. For example, as illustrated in FIG. 8, server 314 may comprise one or more processors 315 and an input/output device 313, which need not be co-located.

Server 314 may, for example, monitor respiration rate, heart rate and activity level of patient 14, e.g., based on signals or information received from IMD 16 and/or programmer 24 via network 312, and compare the monitored levels to predetermined levels to detect worsening heart failure of patient 14 using any of the techniques described herein. Server 314 may provide alerts relating to worsening heart failure of patient 16 via network 312 to patient 14 via access point 310, or to one or more clinicians via computing devices 316. In examples such as those described above in which IMD 16 and/or programmer 24 monitor the respiration rate, heart rate and activity level, server 314 may receive an alert from the IMD or programmer via network 312, and provide alerts to one or more clinicians via computing devices 316. Server 314 may generate web-pages to provide alerts and information regarding diagnostic parameters, and may comprise a memory to store alerts and diagnostic or physiological parameter information for a plurality of patients.

Access point 310 may comprise a device that connects to network 312 via any of a variety of connections, such as telephone dial-up, digital subscriber line (DSL), or cable modem connections. In other embodiments, access point 310 may be coupled to network 312 through different forms of connections, including wired or wireless connections. Network 312 may comprise a local area network, wide area network, or global network, such as the Internet. System 300 may be implemented, in some aspects, with general network technology and functionality similar to that provided by the Medtronic CareLink® Network developed by Medtronic, Inc., of Minneapolis, Minn.

Additionally, using programmers 24, access points 310 or computing devices 316, physicians and/or event patients may input clinical information regarding the patients (such as symptoms, lab results, health care utilizations, etc.). Furthermore, the functionality described herein with respect to monitoring worsening heart failure may be provided by any one or more of the programmers 24, access points 310, server 314, or computing devices 316.

Figure 9A:
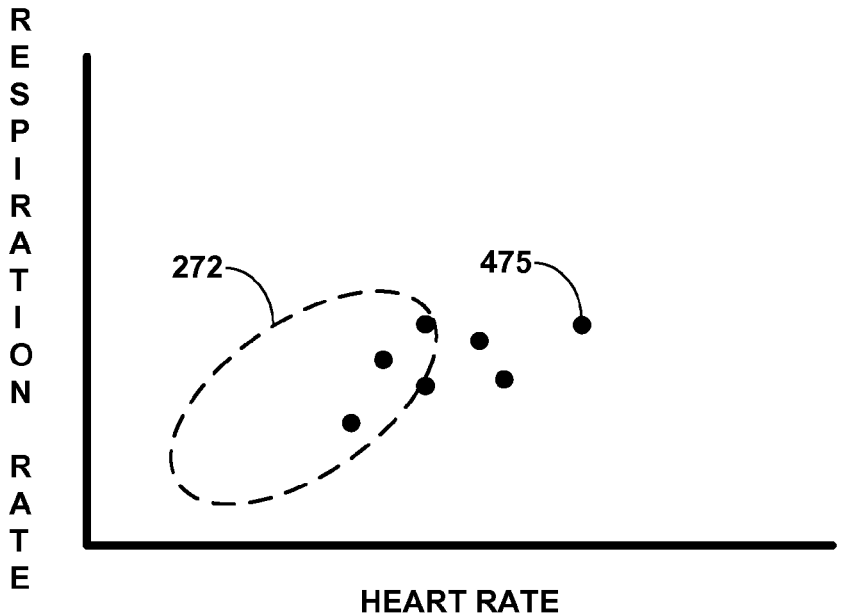
FIGS. 9A-9B are graphical representations of a patient's heart rate and ventilation rate exceeding a predetermined threshold zone for the patient.
Figure 9B:
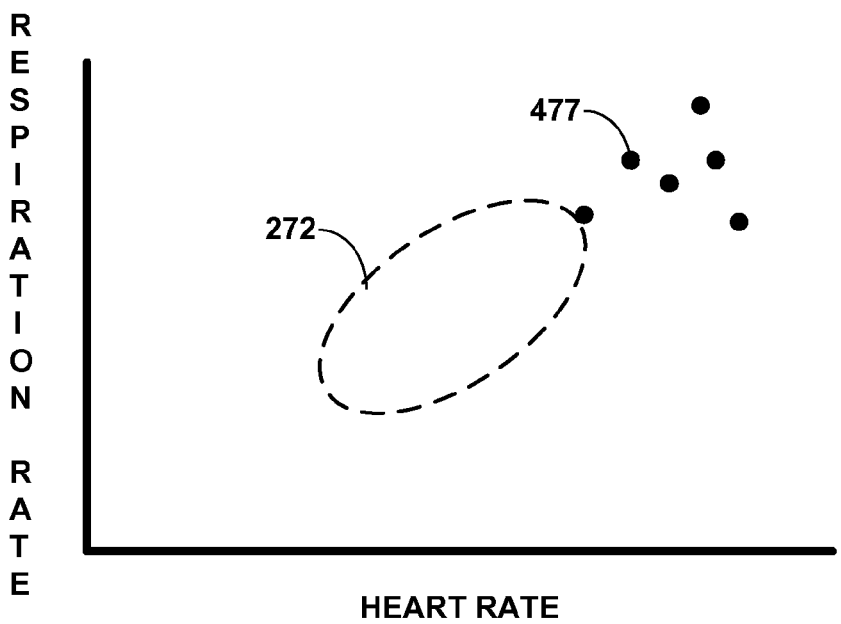

FIGS. 9A-9B are graphical representations of a patient's heart rate and ventilation rate exceeding a predetermined threshold zone for the patient. FIG. 9A illustrates predetermined threshold zone 272 at a sleeping activity level, and FIG. 9B illustrates predetermined threshold zone 272 at a resting activity level. While merely exemplary, predetermined threshold zone 272 is the same as predetermined threshold zone 272 as shown in FIGS. 7A-7D.

In addition, FIG. 9A illustrates a series of data points representing heart rates and respiration rates for a patient at a sleeping activity level. A representative data point in the series is indicated by reference numeral 475. As shown in FIG. 9A, some of the series of data points are outside of predetermined threshold zone 272. This indicates that the patient is experiencing worsening heart failure and that a heart failure event, such as decompensation, may occur. As discussed in greater detail with respect to FIG. 6, an IMD monitoring the heart rate and respiration rate of the patient or a programmer may then issue an alert to the patient or a clinician. The alert may indicate that the patient should receive immediate care to mitigate the worsening heart failure.

Similar to FIG. 9A, FIG. 9B illustrates a series of data points representing heart rates and respiration rates for a patient at a resting activity level. A representative data point in the series is indicated by reference numeral 477. Each some of the series of data points in FIG. 9B are outside of predetermined threshold zone 272. This indicates that the patient is experiencing worsening heart failure and that a heart failure event, such as decompensation, may occur. Accordingly, an alert may be issued indicating that the patient should receive immediate care to mitigate the worsening heart failure.

FIGS. 9A-9B provide example data points in which a patient's respiration rate and heart rate do not correspond to the patient's activity level in that the data points are outside predetermined threshold zone 272. While FIGS. 9A-9B represent instances in which an alert should be issued, it is not necessary for a plurality of data points to be outside predetermined threshold zone 272 before an alert is issued. For example, an alert could be issued if only a single data point occurs outside predetermined threshold zone 272. Other criteria for issuing an alert or for performing any other techniques to mitigate the worsening heart failure may also be used. As previously mentioned, other techniques to mitigate worsening heart failure include, but are not limited to, preparing to deliver a defibrillation pulse to the patient in preparation for a heart failure event, altering drug therapy to the patient, such as delivering diuretics to patient, and/or performing other techniques to mitigate worsening heart failure.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, one of ordinary skill in the art will appreciate that various modifications may be made to the described examples without departing from the scope of the claims. For example, although described primarily with reference to examples that provide an alert in response to detecting worsening heart failure, other examples may additionally or alternatively automatically modify a therapy in response to detecting worsening heart failure in the patient. The therapy may be, as examples, a substance delivered by an implantable pump, cardiac resynchronization therapy, refractory period stimulation, or cardiac potentiation therapy. These and other examples are within the scope of the following claims.

The invention claimed is:

1. A method comprising:
    monitoring a heart rate, a respiration rate and an activity level of a patient;
    comparing the monitored heart rate, respiration rate and activity level to a predetermined threshold zone which is a function of heart rate, respiration rate and activity level;
    determining the patient is experiencing worsening heart failure when the monitored heart rate, respiration rate and activity level are outside the predetermined threshold zone; and
    after determining the patient is experiencing worsening heart failure when the monitored heart rate, respiration rate and activity level are outside the predetermined threshold zone, issuing an alert to indicate that the patient is experiencing worsening heart failure.

2. The method of claim 1, further comprising:
    measuring baseline heart rates and baseline respiration rates at a multitude of activity levels of the patient; and
    calculating the predetermined threshold zone as a function of the measured baseline heart rates and baseline respiration rates for the multitude of activity levels.

3. The method of claim 2, wherein calculating the predetermined threshold zone comprises:
    recording a series of data points corresponding to short term average monitored heart rates, respiration rates and activity levels of the patient; and
    defining the predetermined threshold zone according to the series of data points, wherein the predetermined threshold zone includes a majority of the data points in the series of data points.

4. The method of claim 3, wherein the predetermined threshold zone includes a substantially all of the data points in the series of data points.

5. The method of claim 3, wherein the measuring baseline heart rates and baseline respiration rates comprises recording the series of data points during a plurality of activity levels.

6. The method of claim 5, wherein the plurality of activity levels includes a sleeping activity level and an activity level consistent with exercise.

7. The method of claim 2, wherein the method of claim 2 is performed by an implantable medical device implanted within the patient, wherein the implantable medical device includes:
    one or more accelerometers that outputs acceleration information indicative of the activity level of the patient;
    one or more electrodes that outputs information indicative of the heart rate of the patient and the respiration rate of the patient; and
    a diagnostic unit configured to:
        compare the heart rate, respiration rate and activity level to the predetermined threshold zone, and
        determine the patient is experiencing worsening heart failure when the monitored heart rate, respiration rate and activity level are outside the predetermined threshold zone.

8. The method of claim 1, wherein the predetermined threshold zone is calculated specifically for the patient.

9. The method of claim 1, wherein the method of claim 1 is performed by an implantable medical device implanted within the patient.

10. A medical system for monitoring a condition of a patient comprising:
    one or more sensors configured to output one or more signals indicative of a heart rate, a respiration rate and an activity level of the patient;

a memory configured to store an indication of a predetermined threshold zone which is a function of heart rate, respiration rate and activity level;

a diagnostic unit configured to:
- compare the monitored heart rate, respiration rate and activity level to the predetermined threshold zone, and
- determine the patient is experiencing worsening heart failure when the monitored heart rate, respiration rate and activity level are outside the predetermined threshold zone; and an alert module configured to issue an alert to indicate that the patient is experiencing worsening heart failure after the diagnostic unit determines the patient is experiencing worsening heart failure when the monitored heart rate, respiration rate and activity level are outside the predetermined threshold zone.

11. The medical system for monitoring a condition of a patient of claim 10, further comprising an implantable medical device, wherein the implantable medical device includes the sensors.

12. The medical system for monitoring a condition of a patient of claim 11, wherein the implantable medical device includes the memory and the diagnostic module.

13. The medical system for monitoring a condition of a patient of claim 12, wherein the implantable medical device includes the alert module.

14. The medical system for monitoring a condition of a patient of claim 11, further comprising a programmer, wherein the programmer includes:
- the alert module; and
- a telemetry module configured to communicate wirelessly with the implantable medical device configured to receive information from the implantable medical device that indicates the monitored heart rate, respiration rate and activity level are outside the predetermined threshold zone.

15. The medical system for monitoring a condition of a patient of claim 14, wherein the programmer includes the memory and the diagnostic module.

16. The medical system for monitoring a condition of a patient of claim 11, wherein the implantable medical device is one of a group consisting of:
- a cardiac pacemaker;
- a cardioverters; and
- a defibrillator.

17. The medical system for monitoring a condition of a patient of claim 10, wherein the sensors include:
- one or more accelerometers that outputs acceleration information indicative of the activity level of the patient; and
- one or more electrodes that outputs information indicative of the heart rate of the patient and the respiration rate of the patient.

18. The medical system for monitoring a condition of a patient of claim 10, wherein the predetermined threshold zone was calculated specifically for the patient.

19. A system comprising:
- means for monitoring a heart rate of a patient;
- means for monitoring a respiration rate of the patient;
- means for monitoring an activity level of the patient;
- means for comparing the monitored heart rate, respiration rate and activity level to a predetermined threshold zone which is a function of heart rate, respiration rate and activity level;
- means for determining the patient is experiencing worsening heart failure when the monitored heart rate, respiration rate and activity level are outside the predetermined threshold zone; and
- means for, after determining the patient is experiencing worsening heart failure when the monitored heart rate, respiration rate and activity level are outside the predetermined threshold zone, issuing an alert to indicate that the patient is experiencing worsening heart failure.

20. A non-transitory computer readable storage medium comprising instructions that cause a processor to:
- monitor a heart rate, a respiration rate and an activity level of a patient;
- compare the monitored heart rate, respiration rate and activity level to a predetermined threshold zone which is a function of heart rate, respiration rate and activity level;
- determine the patient is experiencing worsening heart failure when the monitored heart rate, respiration rate and activity level are outside the predetermined threshold zone; and
- after determining the patient is experiencing worsening heart failure when the monitored heart rate, respiration rate and activity level are outside the predetermined threshold zone, issue an alert to indicate that the patient is experiencing worsening heart failure.

* * * * *